United States Patent
Woodard et al.

(10) Patent No.: US 12,274,456 B2
(45) Date of Patent: Apr. 15, 2025

(54) SURGICAL GUIDE AND METHOD OF USE

(71) Applicant: Wright Medical Technology, Inc., Memphis, TN (US)

(72) Inventors: Joseph Woodard, Memphis, TN (US); Paul Luttrell, Germantown, TN (US)

(73) Assignee: WRIGHT MEDICAL TECHNOLOGY, INC., Memphis, TN (US)

(*) Notice: Subject to any disclaimer, the term of this patent is extended or adjusted under 35 U.S.C. 154(b) by 478 days.

(21) Appl. No.: 17/597,747

(22) PCT Filed: Jul. 22, 2020

(86) PCT No.: PCT/US2020/043029
§ 371 (c)(1),
(2) Date: Jan. 21, 2022

(87) PCT Pub. No.: WO2021/025861
PCT Pub. Date: Feb. 11, 2021

(65) Prior Publication Data
US 2022/0313285 A1    Oct. 6, 2022

Related U.S. Application Data (60) Provisional application No. 62/883,196, filed on Aug. 6, 2019.

(51) Int. Cl.
*A61B 17/17*        (2006.01)
*A61B 6/00*         (2006.01)
(Continued)

(52) U.S. Cl.
CPC ............ *A61B 17/1703* (2013.01); *A61B 6/12* (2013.01); *A61B 6/487* (2013.01);
(Continued)

(58) Field of Classification Search
CPC ..... A61B 17/15; A61B 17/17; A61B 17/1703; A61B 17/1775; A61B 2017/320052; A61B 17/90; A61B 2090/3966
See application file for complete search history.

(56) References Cited

U.S. PATENT DOCUMENTS 4,985,019 A * 1/1991 Michelson ........ A61F 13/00051
                                                378/164
5,193,106 A     3/1993 Desena
(Continued)

FOREIGN PATENT DOCUMENTS

WO        2009020764 A1     2/2009

OTHER PUBLICATIONS

Extended European Search Report issued in connection with corresponding European Patent Application No. 20849762.8, Jun. 6, 2023, 8 pages.
(Continued)

*Primary Examiner* — Larry E Waggle, Jr.
(74) *Attorney, Agent, or Firm* — DUANE MORRIS LLP (57) ABSTRACT

A surgical guide and methods of using the surgical guide are disclosed. The surgical guide includes a body having a first side and a second side. An adhesive material is disposed over at least a portion of the first side. A radiopaque guide element coupled to a second side of the body and an incision guard defines an opening extending from the first side to the second side of the body. The incision guard is sized and configured to receive a surgical instrument therethrough such that the incision guard prevents contact between the surgical instrument and a portion of a surgical site adjacent to the opening.

20 Claims, 11 Drawing Sheets

(51) Int. Cl.
*A61B 6/12* (2006.01)
*A61B 17/32* (2006.01)
*A61B 90/00* (2016.01)

(52) U.S. Cl.
CPC ............ *A61B 2017/320052* (2013.01); *A61B 2090/08021* (2016.02); *A61B 2090/3966* (2016.02)

(56) References Cited

U.S. PATENT DOCUMENTS

| | | | |
|---|---|---|---|
| 5,306,271 | A | 4/1994 | Zinreich et al. |
| 5,368,030 | A * | 11/1994 | Zinreich ............... A61B 90/39 324/309 |
| 6,269,148 | B1 | 7/2001 | Jessop et al. |
| 7,326,200 | B2 * | 2/2008 | Trieu ............... A61B 17/7007 606/289 |
| 8,204,575 | B2 * | 6/2012 | Stetz ............... A61B 90/39 600/426 |
| 2008/0021312 | A1 | 1/2008 | Olson et al. |
| 2013/0150703 | A1 | 6/2013 | Buchalter et al. |

OTHER PUBLICATIONS

International Search Report and Written Opinion issued in connection with International Patent Application No. PCT/US2020/043029, Oct. 16, 2020, 15 pages.

* cited by examiner

SURGICAL GUIDE AND METHOD OF USE

CROSS-REFERENCE TO RELATED APPLICATIONS

This application is a National Stage Application, filed under 35 U.S.C. 371, of International Patent Application No. PCT/US2020/043029, filed on Jul. 22, 2020, which claims the benefit of U.S. Patent Application Ser. No. 62/883,196, filed Aug. 6, 2019, the entireties of which are incorporated herein by reference.

BACKGROUND

Current surgical planning and guidance procedures rely on k-wires inserted into a patient, for example, into one or more bones. The k-wires are configured to provide visual guidance for pre-planning and in-situ surgical procedures. K-wires must be inserted into patient's bone or other tissue to mark surgical paths or positions, causing damage to a patient. In addition, k-wires are prone to bending, movement, or dislocation. In some instances, a surgeon must maintain the position of the k-wire manually to prevent movement or dislocation. During pre-planning or execution of a surgical procedure, misplacement of the k-wires requires the k-wires to be removed and reinserted into the patient's anatomy, causing additional tissue damage, increasing recovery times, and increasing risks from the surgery.

During surgical procedures, such as minimally invasive surgical (MIS) procedures, surgeons may pull or push cutting instruments against the perimeter of the incision, causing unwanted contact with tissue surrounding a surgical site. For example, during an MIS osteotomy procedure, a surgeon may push or pull a burr in a direction perpendicular to the axis of the burr, bringing the rotating burr into contact with skin and other tissue around the surgical site, resulting in heating and/or tearing of the tissue. Although k-wires can provide guidance for surgical instruments, k-wires are not able to prevent undesirable contact between instruments and surrounding tissue.

SUMMARY

In various embodiments, a surgical guide is disclosed. The surgical guide includes a body having a first side and a second side. An adhesive material is disposed over at least a portion of the first side. A radiopaque guide element is coupled to a second side of the body and an incision guard defines an opening extending from the first side to the second side of the body. The incision guard is sized and configured to receive a surgical instrument therethrough and is configured to prevent contact between the surgical instrument and a portion of a surgical site adjacent to the opening.

In various embodiments, a system is disclosed. The system includes a surgical guide carrier, a first surgical guide coupled to the surgical guide carrier in a first position, and a second surgical guide coupled to the surgical guide carrier in a second position. The first surgical guide includes a body having a first side and a second side, an adhesive material disposed over at least a portion of the first side, a radiopaque guide element coupled to a second side of the body, and an incision guard defining an opening extending from the first side to the second side of the body. The incision guard is sized and configured to receive a surgical instrument therethrough such that the incision guard prevents contact between the surgical instrument and a portion of a surgical site adjacent to the opening. The second surgical guide includes a body having a first side and a second side, an adhesive material disposed over at least a portion of the first side, and a radiopaque guide element coupled to a second side of the body.

In various embodiments, a method is disclosed. The method includes a step of removing a first surgical guide from a carrier. The first surgical guide includes a body having a first side including an adhesive material disposed over at least a portion thereof and a second side, a radiopaque guide element coupled to a second side of the body, and an incision guard defining an opening extending from the first side to the second side of the body sized and configured to receive a cutting instrument therethrough. The first surgical guide is coupled to a surgical site and a fluoroscopic image of the first surgical site including the first surgical guide is obtained. A surgical instrument is inserted through the incision guard to perform at least one surgical procedure. The incision guard is configured to prevent contact between the surgical instrument and a portion of the surgical site located adjacent to the opening defined by the incision guard.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Various embodiments of surgical guides and methods of use are disclosed. In some embodiments, a surgical guide includes a body defining a first side and a second side. An adhesive material is disposed over at least a portion of the first side. An incision guard defines an opening extending from the first side to the second side of the body. The incision guard is sized and configured to receive a surgical instrument therethrough. In some embodiments, the incision guard is defined by an eyelet extending about the circumference of the opening. The eyelet is configured to provide reinforcement to the body of the surgical guide. The incision guard prevents contact between the surgical instrument inserted through the opening and a portion of a surgical site positioned outside of the circumference of the opening. In some embodiments, the surgical guide includes one or more radiopaque guide elements formed on at least the second side of the body. The radiopaque guide elements are configured to provide pre-operative and/or intra-operative guidance.

Figure 1:
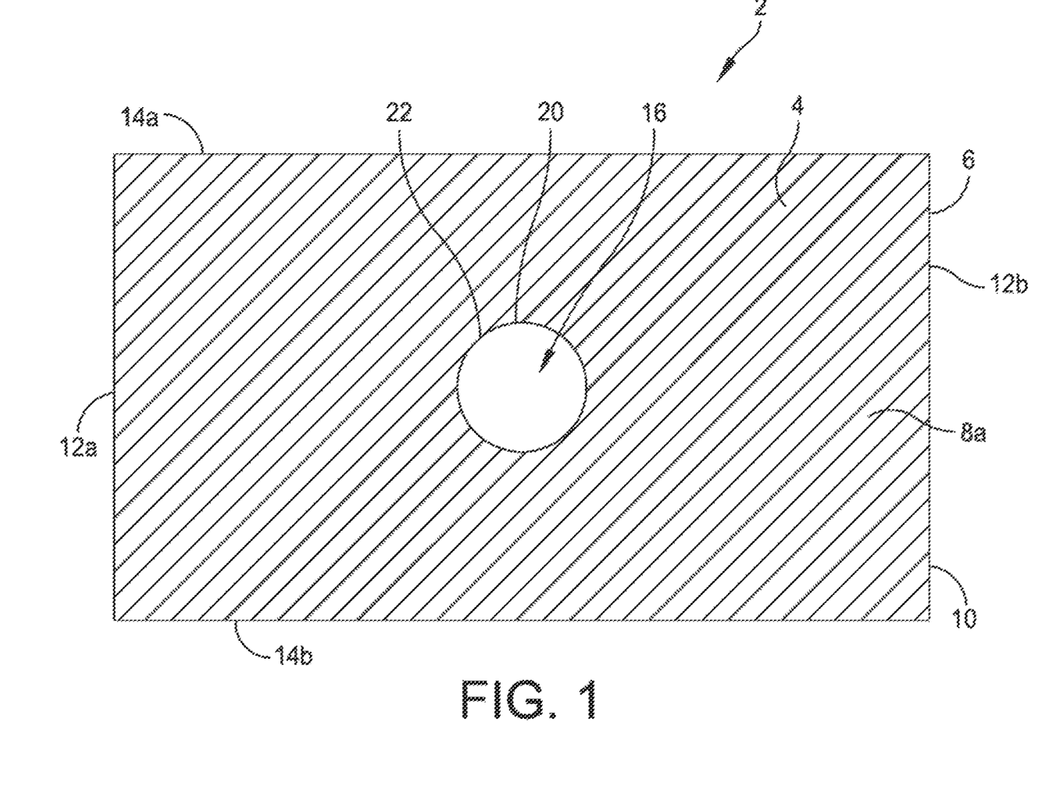
FIG. 1 illustrates a surgical guide including a first side having an adhesive disposed thereon and an incision guard sized and configured to receive an instrument therethrough, in accordance with some embodiments.
Figure 2:
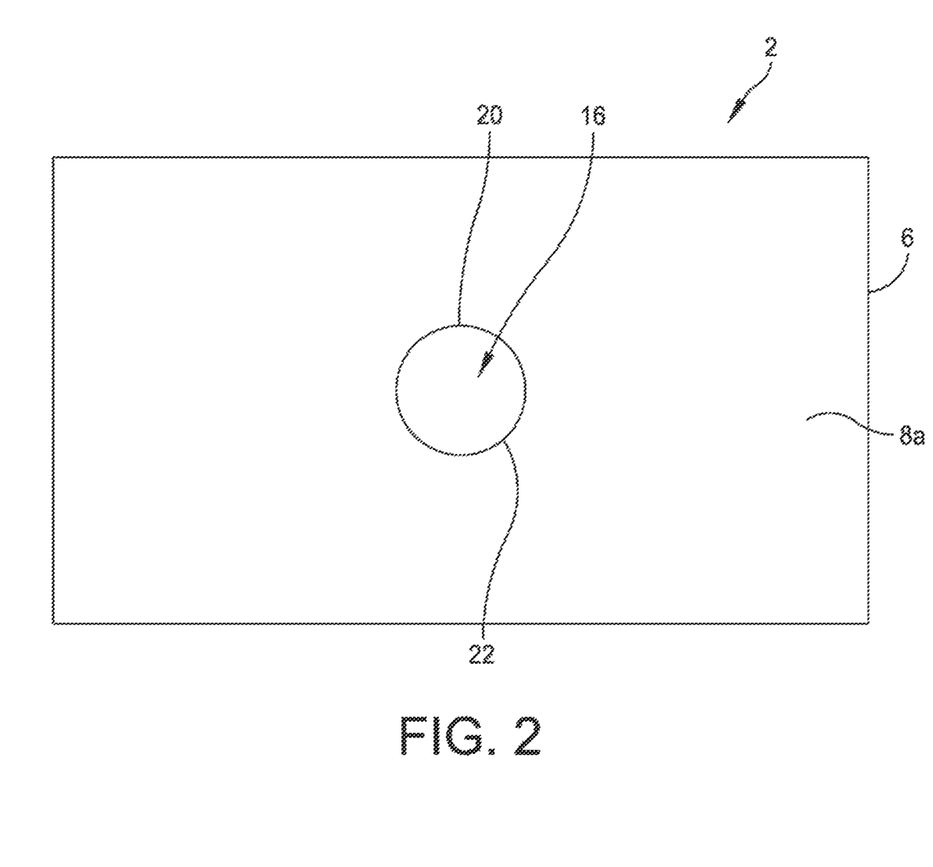
FIG. 2 illustrates a second side of the surgical guide of FIG. 1, in accordance with some embodiments.

FIGS. 1 and 2 illustrate a surgical guide 2 including an incision guard 20 sized and configured to receive a surgical instrument therethrough, in accordance with some embodiments. The surgical guide 2 includes a body 6 defined by a first side 8a, a second side 8b, and a perimeter 10. In the illustrated embodiment, the perimeter 10 includes a first set of parallel sides 12a, 12b and a second set of a parallel sides 14a, 14b defining a rectangular shape. Although specific embodiments are illustrated herein, it will be appreciated that the body 10 can include any suitable shape, such as, for example, a geometric (e.g., circular, square, triangular, etc.) and/or non-geometric shape.

An adhesive material 4 is disposed over at least a portion of the first side 8a and/or the second side 8b of the body 6. The adhesive material 4 is configured to couple the surgical guide 2 to a surface, such as, for example, the skin of a patient. The adhesive material 4 can include any suitable adhesive material, such as, for example, an Acrylic/Acrylate adhesive, silicone elastomer adhesive, a synthetic rubber, and/or any other suitable medical adhesive material.

In some embodiments, the adhesive material 4 is disposed over the entire surface area of the first side 8a. In other embodiments, the adhesive material 4 may be disposed over a majority, a minority, a perimeter, and/or any other predetermined portion of the first side 8a. In some embodiments, a backing material (not shown) is coupled to the adhesive material 4 of the surgical guide 2. The backing material is configured to prevent the adhesive material 4 from interacting with other surfaces until the surgical guide 2 is ready to be applied to a predetermined surface, such as a surgical site. The backing material may include a material configured to be easily removed from the adhesive material 4. In some embodiments, the backing material includes a surgical guide carrier configured to carry two or more surgical guides, such as the surgical guide carriers 200, 300 discussed in greater detail below. In other embodiments, the adhesive material 4 is exposed and/or is coupled to one or more carrier materials, such as a continuous strip, sheet, and/or other carrier material, as discussed in greater detail below.

In some embodiments, the surgical guide 2 includes an incision guard 20 defining an opening 16 extending from the first side 8a to a second side 8b of the body 6. The opening 16 is sized and configured to receive a surgical instrument, such as a drill bit, burr, saw, reciprocating rasp, and/or other surgical instrument therethrough. The opening 16 is sufficiently sized to allow insertion of the surgical instrument through the incision guard 20 without contact between the surgical instrument and the incision guard 20.

The incision guard 20 is configured to prevent accidental and/or unintended contact between a surgical instrument inserted through the opening 16 and a portion of a surgical site positioned outside of the perimeter of the incision guard 20. For example, when using a burr or other cutting instrument, an access incision or port may be collocated with the opening 16. The burr is inserted through the incision guard 20 to form a bone cut and/or perform other surgical operations. If the surgeon applies an accidental and/or unintended pushing or pulling force, the incision guard prevents contact between the shaft of the burr (in rotation during cutting) and a portion of the surgical site (e.g., skin) positioned adjacent to the surgical incision. By preventing unintended/accidental contact, the incision guard 20 prevents heating (burning) or tearing of the surgical site. The incision guard 20 is maintained in a fixed position by the body 6 and prevents the burr from traveling laterally with respect to the axis of insertion.

In some embodiments, the incision guard 20 includes an eyelet 22 extending about and/or defining the perimeter of the opening 16. The eyelet 22 may be coupled to the body 6 using any suitable coupling mechanism, such as, for example, crimping, adhesive, ultrasonic welding, etc. The eyelet 22 can include any suitable material, such as, for example, a metal material (e.g., stainless steel), ceramic, and/or any other suitable material.

In some embodiments, the body 6 of the surgical guide 2 is made from and/or includes a material configured to provide additional strength and/or resilience to the opening 16. The body 6 may include one or more of a metal material, a plastic material, a rubber material, and/or any other material configured to provide strength and/or resilience to the body 6 and/or the opening 16. In some embodiments, the eyelet 22 and the body 6 include similar materials. In some embodiments, the eyelet 22 is omitted and the incision guard 20 includes a portion of the body 6, such as, for example, a reinforced portion, portion having an increased thickness, etc.

In various embodiments, the surgical guide 2 is configured to be coupled to a surgical site. The surgical guide 2 may be configured to provide targeting and/or guidance to a surgeon for insertion of a surgical instrument and/or to prevent unintended movement of and/or contact by a surgical instrument during a surgical procedure. In some embodiments, the eyelet 22 includes a radiopaque material configured to provide imaging guidance prior to and/or during a surgical procedure. The surgical site, including the surgical guide 2, may be imaged using any suitable imaging methodology, such as, for example, fluoroscopy. The radiopaque material of the eyelet 22 allows a surgeon to compare placement of the eyelet 22 (and by extension, the surgical guide 2), prior to insertion of a surgical instrument. For example, the surgeon may confirm that the opening 16 defined by the incision guard is co-located with a bone to be cut using a surgical instrument. If the eyelet 22 is not positioned in a desirable location, the surgeon may remove the surgical guide 2 from the surgical site and reposition the surgical guide 2 at the desired location. In some embodiments, and as discussed in greater detail below, the surgical guide 2 may include one or more radiopaque guide elements (see, for example, FIGS. 4-7) configured to provide additional and/or alternative guidance and/or imaging during a surgical procedure.

Figure 3:
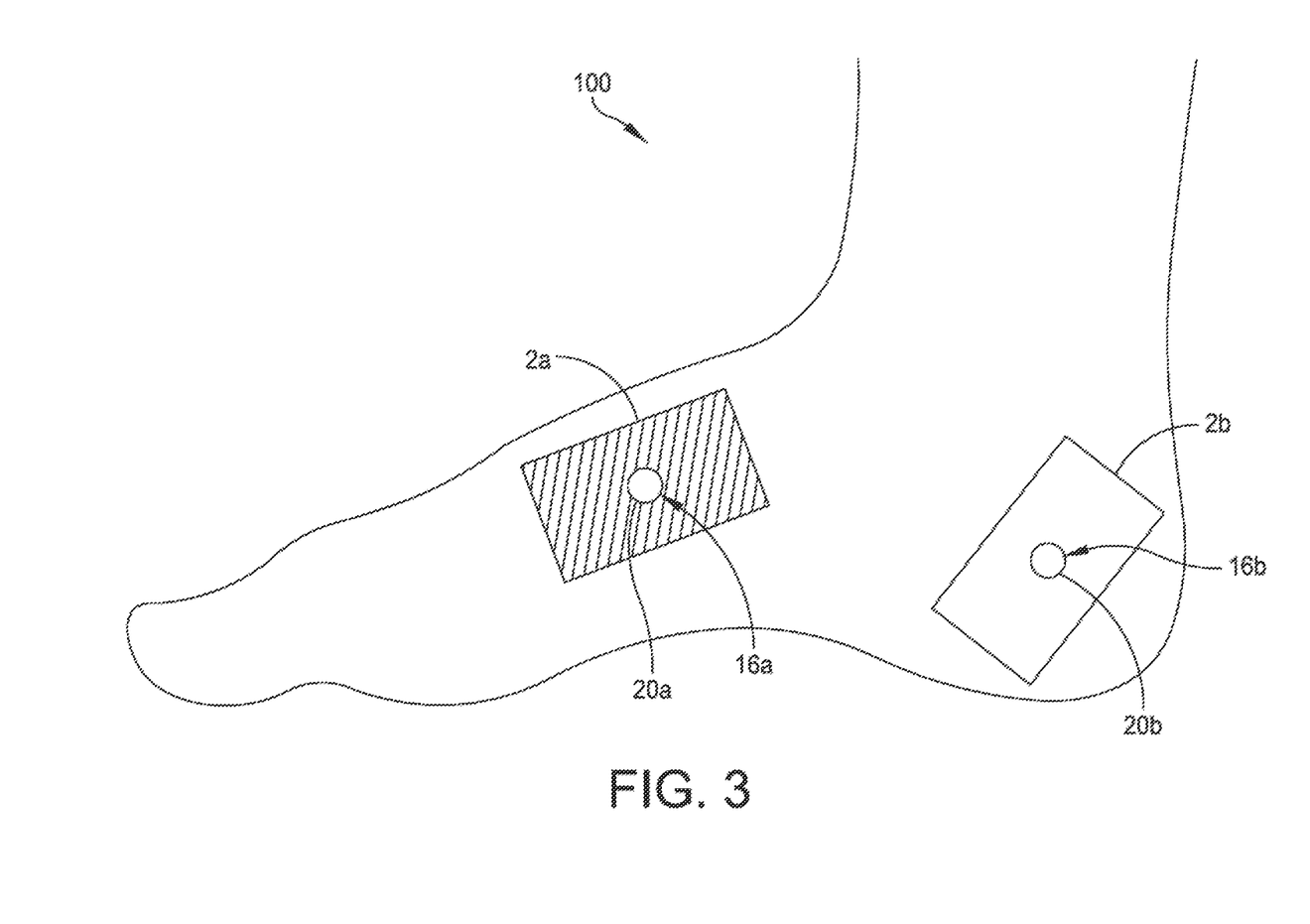
FIG. 3 illustrates a first surgical guide defining a first incision guard coupled to a first surgical site and a second surgical guard defining a second incision guard coupled to a second surgical site, in accordance with some embodiments.

FIG. 3 illustrates a surgical guide 2*a* including a first incision guard 20*a* and a second surgical guide 2*b* defining a second incision guard 20*b* each coupled to a foot 100 of a patient, in accordance with some embodiments. Each of the surgical guides 2*a*, 2*b* are configured to direct a surgical instrument inserted through a respective incision guard 20*a*, 20*b* to a predetermined position within the foot 100. For example, in the illustrated embodiment, the first surgical guide 2*a* includes an opening 16*a* configured to direct a surgical instrument to perform, for example, a cutting operation during a TMT fusion and the second surgical guide 2*b* includes an opening 16*b* configured to direct a surgical instrument to perform, for example, a cutting operation during a calcaneal osteotomy. Although embodiments are discussed herein with surgical guides 2*a*, 2*b* positioned with respect to specific surgical procedures, it will be appreciated that the surgical guides 2*a*, 2*b* can be positioned at any surgical site for any suitable surgical procedure.

Each of the openings 16*a*, 16*b* on each respective surgical guide 2*a*, 2*b* includes an incision guard 20*a*, 20*b* configured to prevent accidental and/or unintended contact between a surgical instrument inserted through the opening 16 and a portion of the surgical site located outside of the respective opening 16*a*, 16*b*. In the illustrated embodiment, the first opening 16*a* includes an incision guard 20*a* sized and configured to receive a first burr for performing a cutting step of a distal osteotomy of a first ray and the second opening 16*b* includes an incision guard 20*b* sized and configured to receive a second burr (or other cutting instrument) for performing a cutting step of a calcaneal osteotomy. Although embodiments are illustrated including a single incision guard 20*a*, 20*b* on each respective surgical guide 2*a*, 2*b*, it will be appreciated each surgical guide 2*a*, 2*b* can include zero, one, two, or more incision guards 20*a*, 20*b*.

Figure 4:
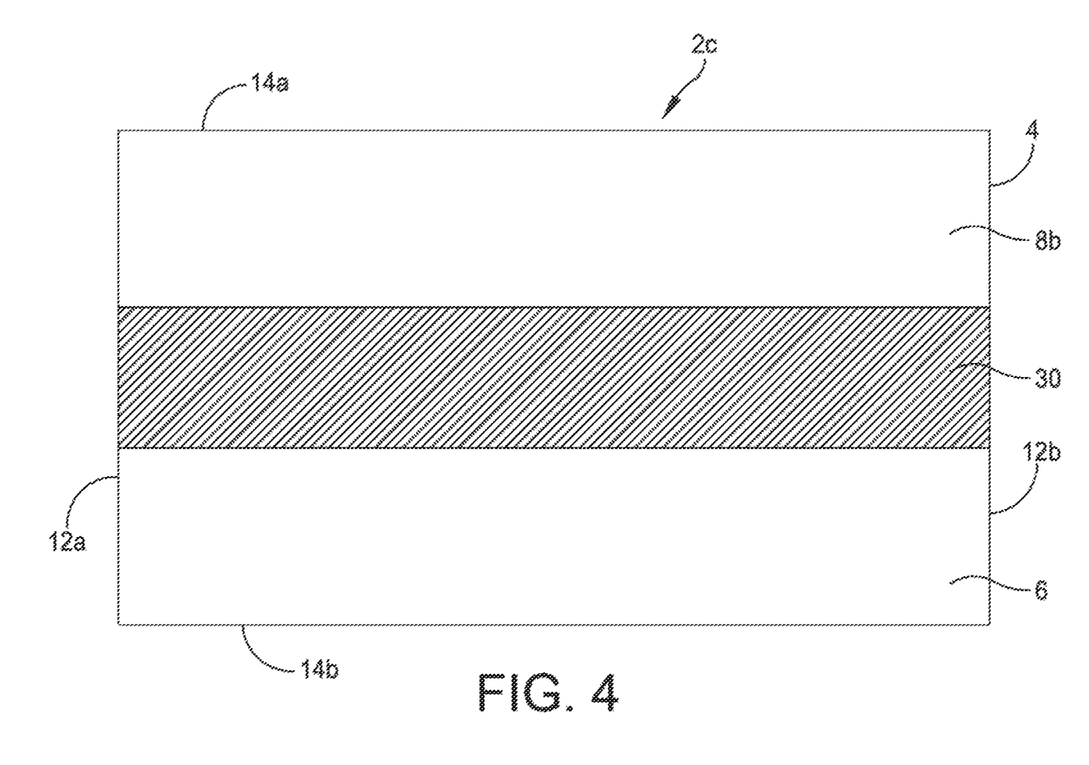
FIG. 4 illustrates a surgical guide including a radiopaque guide element configured to be positioned relative to at least one anatomical structure, in accordance with some embodiments.

FIG. 4 illustrates a surgical guide 2*c* including a radiopaque guide element 30, in accordance with some embodiments. The surgical guide 2*c* is similar to the surgical guides 2-2*b* discussed above, and similar description is not repeated herein. The radiopaque guide element 30 is configured to be positioned relative to and provide a guide reference with respect to at least one surgical site and/or anatomical structure. For example, in various embodiments, the radiopaque guide element 30 may correspond to an access incision location or path, a bone cutting location or path (e.g., an osteotomy location), an initial surgical position, a final surgical position, and/or any other suitable reference positions corresponding to one or more surgical procedures. The radiopaque guide element 30 includes a radiopaque material, such as a radiopaque ink and/or other radiopaque material, formed on and/or integrally with the body 6 of the surgical guide 2*c*. For example, in some embodiments, the radiopaque guide element 30 includes a radiopaque ink disposed on a second side 8*b* of the body 6. Although specific embodiments are discussed herein, it will be appreciated that the radiopaque guide element 30 can include radiopaque material formed on and/or integrally with any surface of the body 6.

In some embodiments, the radiopaque guide element 30 is used to plan and/or guide a surgical operation, such as, for example, an osteotomy. The surgical guide 2*c* is coupled to a surgical site, for example, a patient's foot or other extremity, to assist in planning and/or performance of a surgical operation. The surgical guide 2*c* is coupled to the surgical site such that the radiopaque guide element 30 marks and/or corresponds to the location of a planned surgical operation, such as an incision, osteotomy, and/or other surgical operation. An image, such as an x-ray (e.g., fluoroscopic) image, nuclear image, and/or other medical image, may be taken to confirm the position of the surgical guide 2*c* and/or the radiopaque guide element 30 with respect to one or more anatomical structures of the surgical site. If the surgical guide 2*c* is not positioned at a desired location with respect to the one or more anatomical structures, the surgical guide 2*c* may be removed from the patient and repositioned.

In some embodiments, after confirming the position of the radiopaque guide element 30, the surgical guide 2*c* may be used as a visual indicator and/or position marker during one or more surgical procedures, such as formation of an incision or an osteotomy. The surgical procedure may be performed by following a portion of the surgical guide 2*c*, such as an edge of the surgical guide 2*c*, the radiopaque guide element 30, and/or any other portion of the surgical guide 2*c*. In some embodiments, the surgical guide 2*c* may be removed prior to, during, and/or after one or more surgical operations are performed.

In some embodiments, the use of a surgical guide including a radiopaque guide element 30 eliminates the need to insert k-wires or other guide elements into a patient for surgical planning or guidance. K-wires must be inserted into patient's bone or other tissue to mark surgical paths or positions and may be prone to bending, movement, or dislocation. In some instances, a surgeon must maintain the position of the k-wire manually to prevent movement or dislocation. In addition, relocation of the k-wire based on fluoroscopy results in additional injury to a patient. In contrast, by using a surgical guide 2*c* including a radiopaque guide element 30, the surgeon can affix the surgical guide 2*c* to a patient without causing damage to tissue and can easily relocate the surgical guide 2*c* as needed. In addition, the adhesive nature of the surgical guide 2*c* provides hands free guidance and planning to the surgeon, freeing both of the surgeon's hands for use during a procedure. This and other advantages of the surgical guide 2*c* will be apparent to those of ordinary skill in the art.

Figure 5:
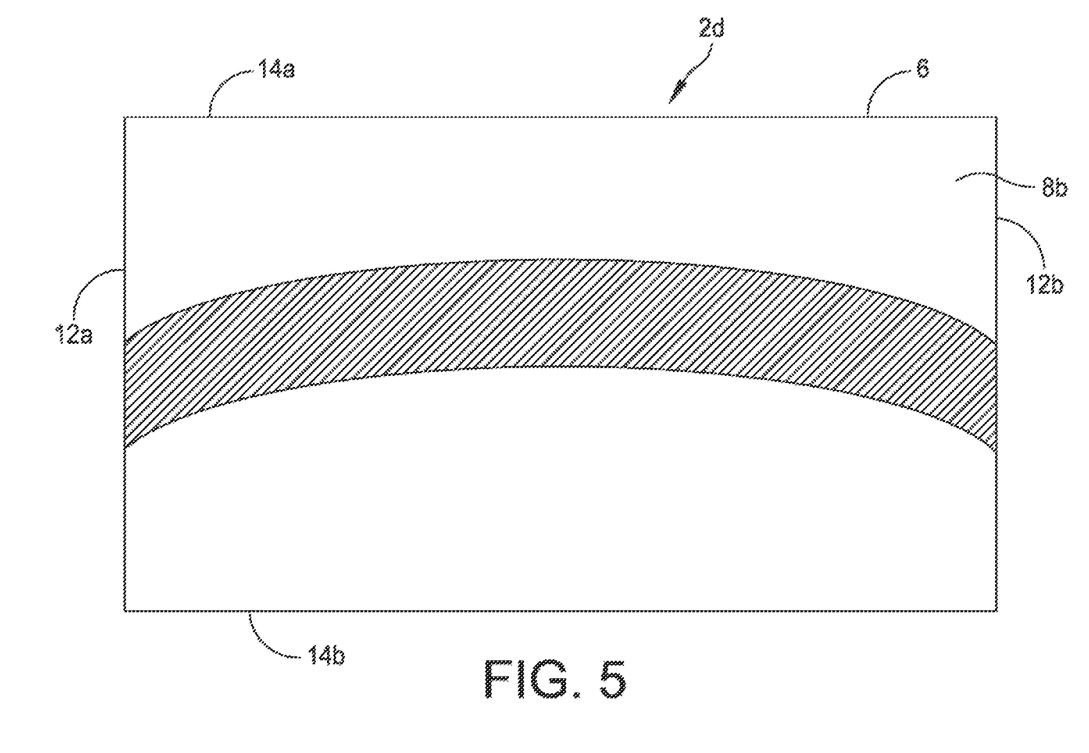
FIG. 5 illustrates a surgical guide including a curved radiopaque guide element, in accordance with some embodiments.

FIG. 5 illustrates a surgical guide 2*d* including a curved radiopaque guide element 30*a*, in accordance with some embodiments. The surgical guide 2*d* is similar to the surgical guide 2*c* described above, and similar description is not repeated herein. The curved radiopaque marker 30*a* includes a curved or arcuate path extending over a second surface 8*b* of the body 6. The curved radiopaque guide element 30*a* can include any suitable continuous and/or discontinuous curve extending over any portion of the surgical guide 2*d*. For example, in the illustrated embodiment, the curved radiopaque guide element 30*a* includes a continuous curved path extending from a first edge 12*a* of the surgical guide 2*d* to a second edge 12*b*. In some embodiments, the curved radiopaque guide element 30 may include multiple curved paths extending over separate portions of the surgical guide 2d.

Figure 6:
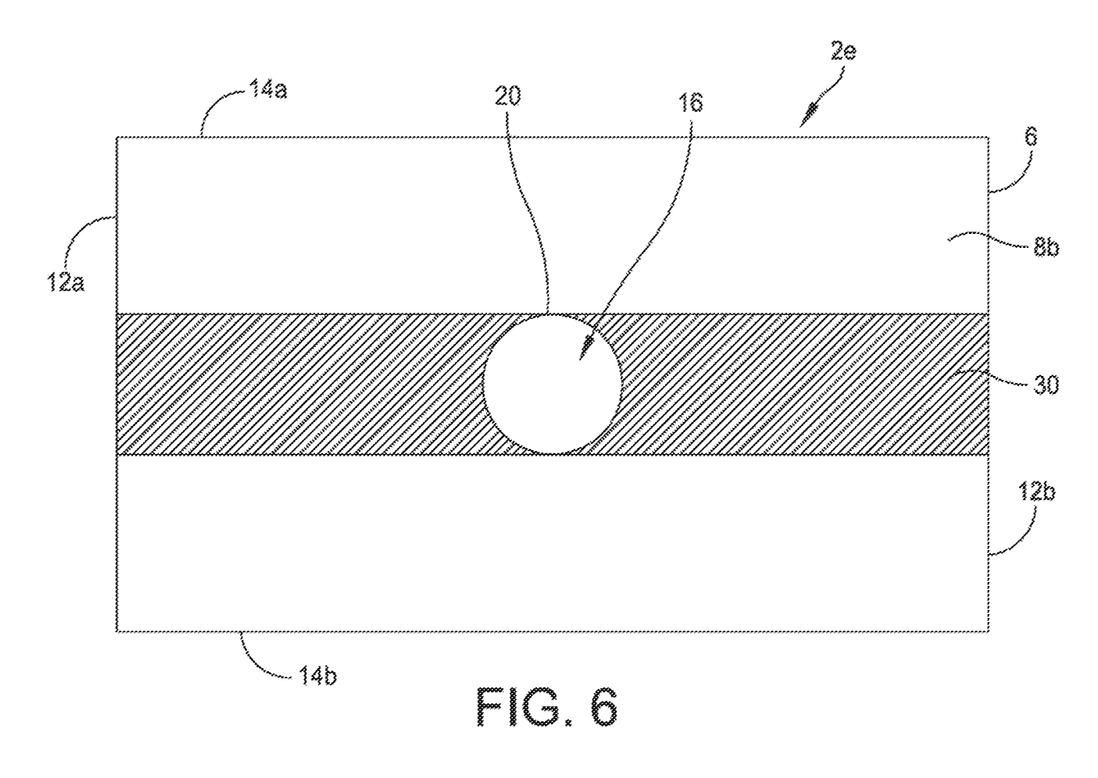
FIG. 6 illustrates a surgical guide including a radiopaque marker and an incision guard, in accordance with some embodiments.

FIG. 6 illustrates a surgical guide 2e including a radiopaque guide element 30 and an incision guard 20, in accordance with some embodiments. The surgical guide 2e is similar to the surgical guides 2-2d described above, and similar description is not repeated herein. The surgical guide 2e includes an incision guard 20 defining a discontinuity or break in the radiopaque guide element 30. In the illustrated embodiment, the incision guard 20 is positioned at a center of the radiopaque guide element 30, although it will be appreciated that the incision guard 20 can be positioned to form a discontinuity at any portion of the radiopaque guide element 30. In some embodiments, the incision guard 20 may be offset from the radiopaque guide element 30 to provide a continuous radiopaque guide element 30 and an incision guard 20.

In some embodiments, the incision guard 20 corresponds to an insertion point for a surgical instrument used during a surgical procedure corresponding to a position of the radiopaque guide element 30. For example, in some embodiments, the incision guard 20 may be sized and configured to receive a burr or other cutting instrument therethrough. The burr may be pivoted within the incision guard 20 to provide a bone cut extending substantially parallel to the radiopaque guide element 30. In some embodiments, the surgical guide element 30 may be used only in a planning phase of a surgical procedure, for example, to ensure proper positioning of the incision guard 20 prior to insertion of a cutting instrument.

Figure 7:
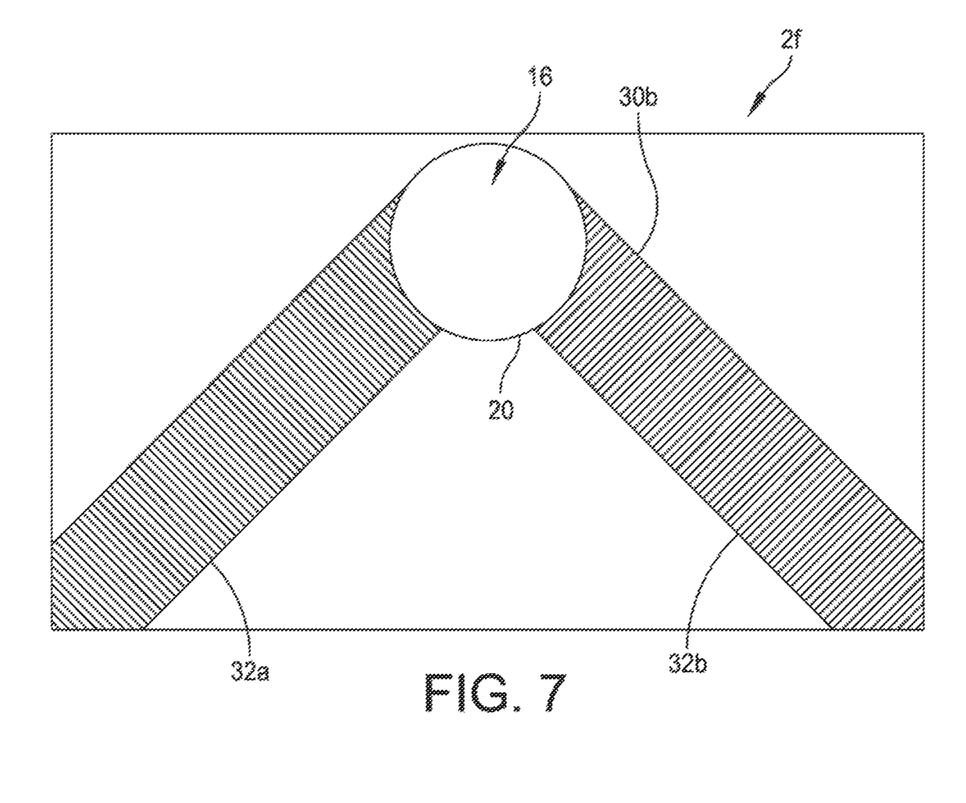
FIG. 7 illustrates a surgical guide defining an angled radiopaque guide element and an incision guard, in accordance with some embodiments.

FIG. 7 illustrates a surgical guide 2f including an angled (or multi-plane) radiopaque guide element 30b and an incision guard 20, in accordance with some embodiments. The surgical guide 2f is similar to the surgical guides 2-2e described above, and similar description is not repeated herein. The surgical guide 2f includes an incision guard 20 located at the apex (or intersection) of angled portions of the radiopaque guide element 30b. For example, in the illustrated embodiment, a first portion 32a of the radiopaque guide element 30b and a second portion 32b of the radiopaque guide element 30b intersect at a predetermined angle. It will be appreciated that the angle of intersection between the first portion 32a and the second portion 32b can include any angle between 0-180°, such as, for example, any angle between 0-90°, any angle between 10-170°, any angle between 30-120°, etc. The angle of intersection may correspond to an angle between and/or formed by one or more anatomical structures at the surgical site. In the illustrated embodiments, the incision guard 20 is positioned at the intersection between the first portion 32a and the second portion 32b, although it will be appreciated that the incision guard 20 can be positioned at any portion of the radiopaque guide element 30b and/or at any portion of the surgical guide 2f.

Figure 8:
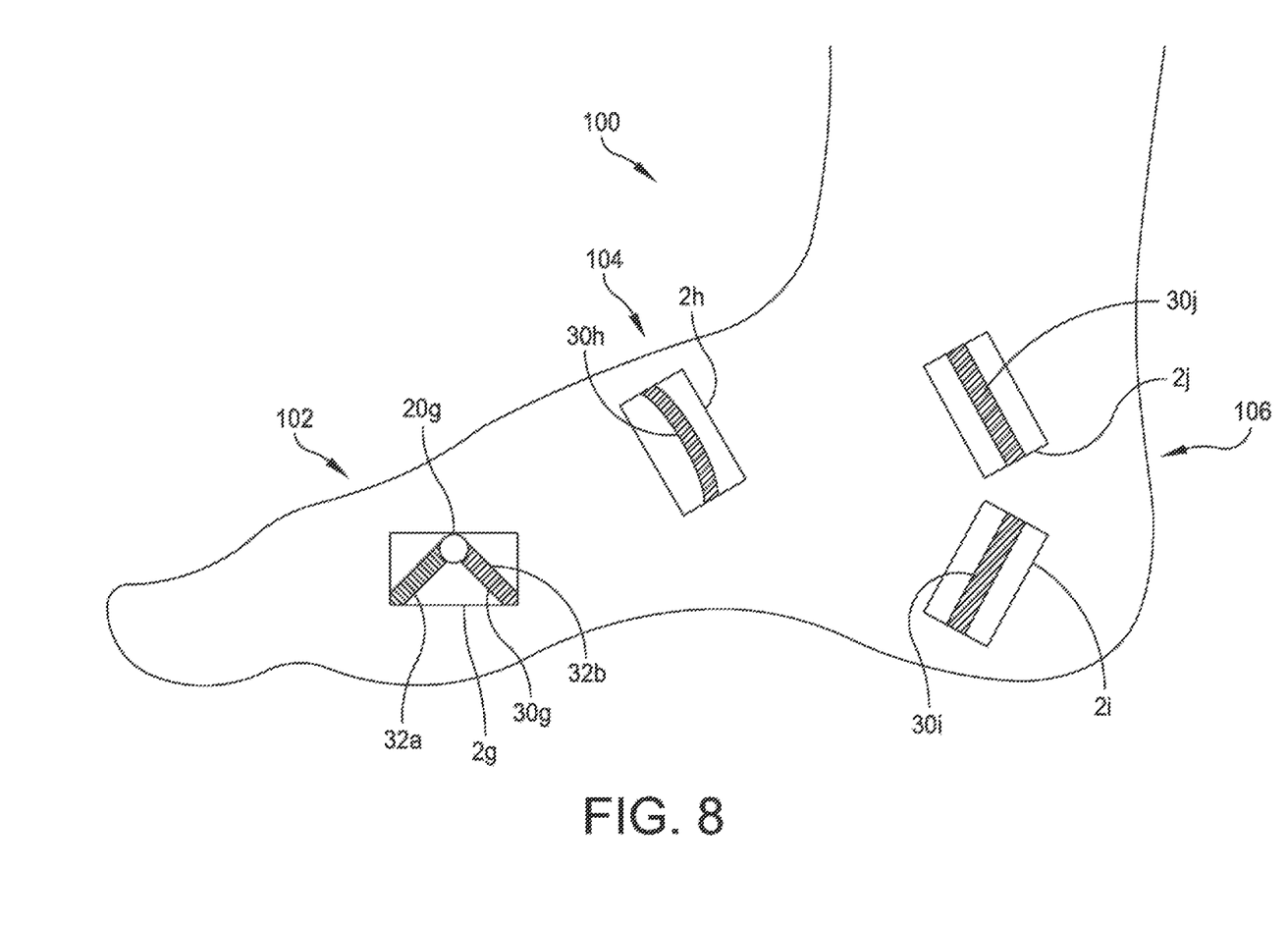
FIG. 8 illustrates a plurality of surgical guides configured for surgical planning and/or surgical guidance, in accordance with some embodiments.

FIG. 8 illustrates a patient's foot 100 including a plurality of surgical guides 2g-2j configured to provide surgical planning and/or surgical guidance at a plurality of surgical sites 102-106, in accordance with some embodiments. Each of the surgical guides 2g-2j are similar to the surgical guides 2-2f described above, and similar description is not repeated herein. A first surgical guide 2g is coupled to an anterior portion 102 of a patient's foot 100. The first surgical guide 2g includes a first radiopaque guide element 30g and an incision guard 20g. The first radiopaque guide element 30g includes a first portion 32a and a second portion 32b disposed at a predetermined angle. The first surgical guide 2g is coupled to the surgical site 102 in a position corresponding to a distal metatarsal osteotomy. The first incision guard 20g extends through the intersection of the first portion 32a and the second portion 32b of the radiopaque guide element 30g and corresponds to a location of insertion for a burr to perform at least a portion of a distal metatarsal osteotomy.

A second surgical guide 2h is coupled to a mid-section 104 of the patient's foot 100. The second surgical guide 2h includes a second radiopaque guide element 30h corresponding to a location for a TMT fusion operation. The second radiopaque guide element 30h includes a curved, or arcuate, path. The second surgical guide 2h provides hands-free guidance to a surgeon when performing one or more portions of the TMT fusion procedure, such as, an initial incision and/or osteotomy.

A third surgical guide 2i and a fourth surgical guide 2j are coupled to a posterior portion 106 of the patient's foot 100. Each of the third surgical guide 2i and the fourth surgical guide 2j include radiopaque guide elements 30i, 30j corresponding to various portions of a calcaneal osteotomy. Each of the radiopaque guide elements 30i, 30j include generally straight guide elements configured to illustrate and/or guide an incision and/or bone cutting operation during a calcaneal osteotomy. Although two surgical guides 2i, 2j are illustrated, it will be appreciated that any number of surgical guides 2i, 2j can be used for planning a single surgical procedure, such as, for example, one, two, three, or more surgical guides. Further, it will be apparent that the two surgical guides 2i, 2j may be replaced with a single surgical guide including an angled radiopaque guide element having a first portion and a second portion disposed at an angle similar and/or equal to the angle between the radiopaque guide elements 30i, 30j illustrated in FIG. 8.

Figure 9:
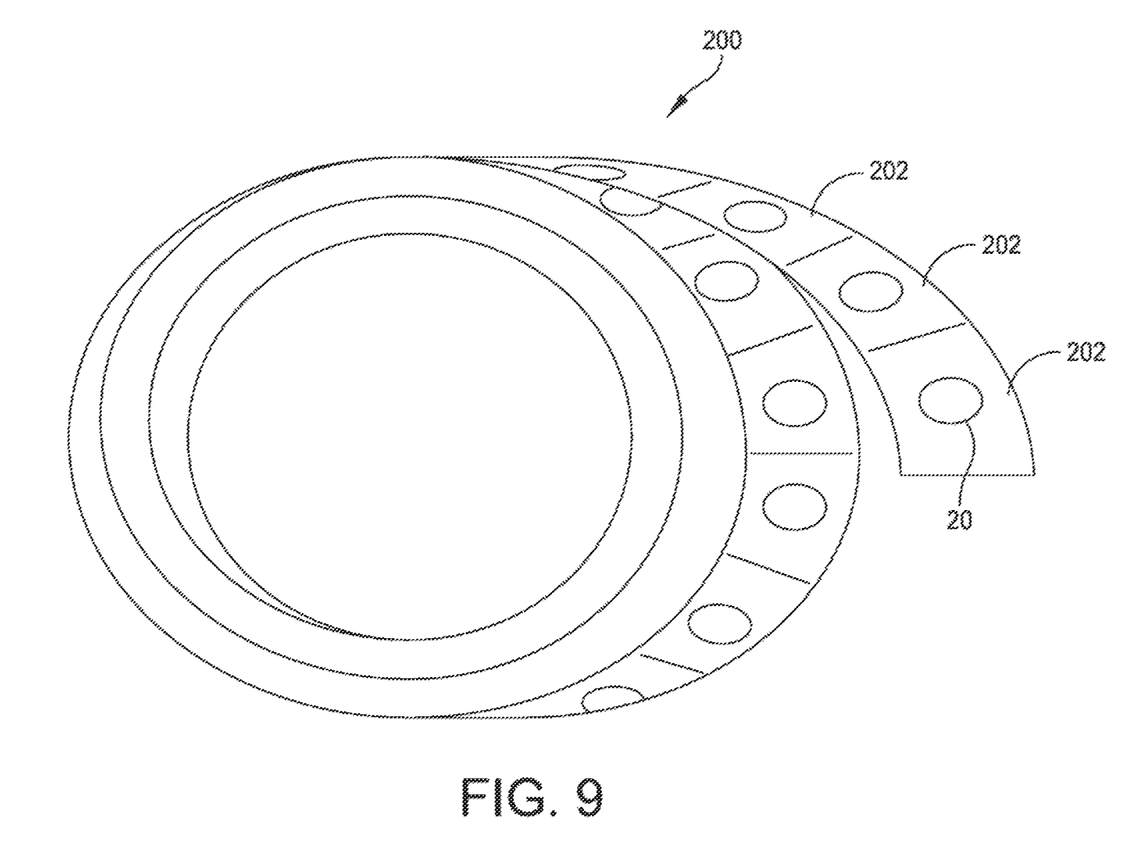
FIG. 9 illustrates a continuous roll guide carrier including a plurality of surgical guides each defining at least one incision guard, in accordance with some embodiments.

FIG. 9 illustrates a continuous roll guide carrier 200 containing a plurality of surgical guides 202 each including at least one incision guard 20, in accordance with some embodiments. The surgical guides 202 are similar to the surgical guides 2-2j discussed above, and similar description is not repeated herein. The continuous roll guide carrier 200 includes a predetermined number of surgical guides 202 configured to be separated and affixed to a surgical site as needed. The continuous roll guide carrier 200 may include surgical guides 202 having an adhesive on a first side covered by a removable backing configured to protect the adhesive until use and/or protected by subsequent surgical guides 202 in the continuous roll guide carrier 200. The continuous roll guide carrier 200 may be precut to define each surgical guide 202 and/or may be cut prior to and/or during a surgical operation to define one or more surgical guides 202 having one or more incision guards 20.

Figure 10:
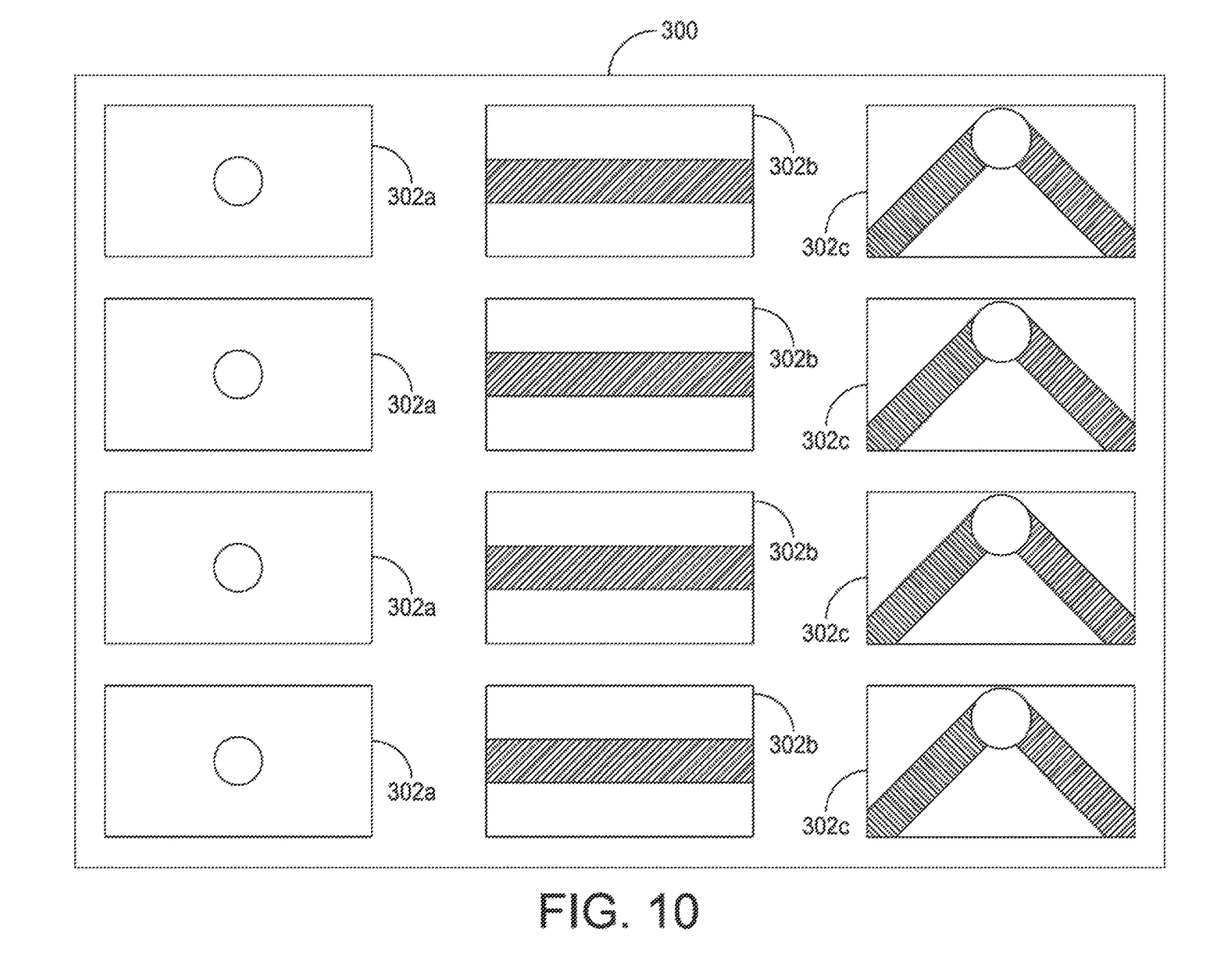
FIG. 10 illustrates a sheet guide carrier including a plurality of surgical guides each defining at least one incision guard, in accordance with some embodiments.

FIG. 10 illustrates a sheet guide carrier 300 containing a plurality of surgical guides 302a-302d, in accordance with some embodiments. The surgical guides 302 are similar to the surgical guides 2-2j, 202 discussed above, and similar description is not repeated herein. Each of the surgical guides 302a-302d includes a surface having an adhesive at least partially formed thereon. The adhesive adheres the surgical guide 302 to the sheet guide carrier 300. A surgeon may remove one or more of the surgical guides 302a-302d prior to and/or during a surgical procedure and affix the surgical guide 302a-302d to a patient. In some embodiments, the plurality of surgical guides 302a-302d included on a sheet guide carrier 300 may correspond to a single surgical procedure and may each be configured to be affixed to a patient at a predetermined location. In other embodiments, a sheet guide carrier 300 may include surgical guides 302a-302d corresponding to multiple surgical procedures (such as a set of surgical procedures) and/or generic surgical guides 302a-302d usable for any one of a set of surgical procedures.

Figure 11:
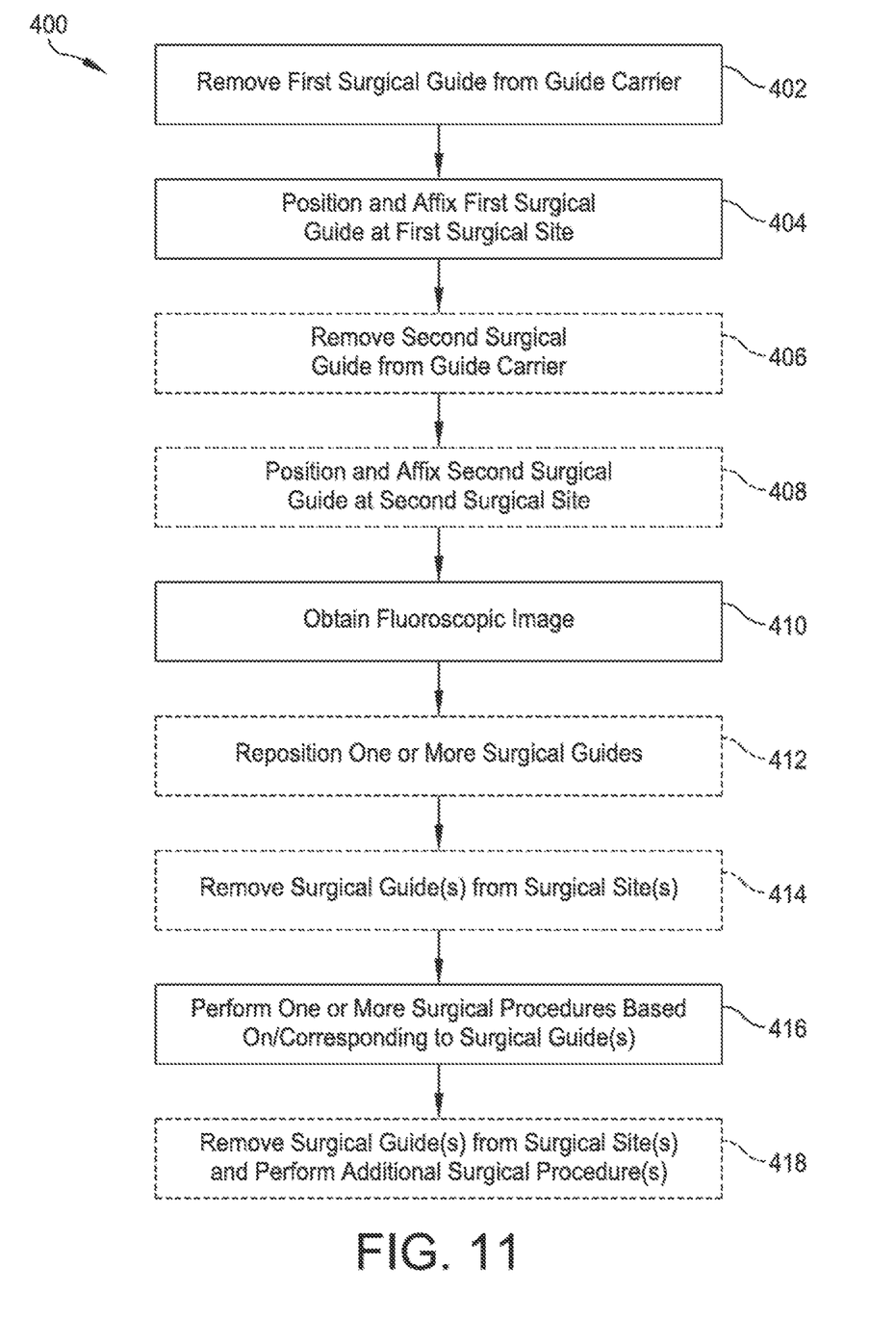
FIG. 11 is a flowchart illustrating method of planning and performing a surgical procedure using at least one surgical guide, in accordance with some embodiments.

FIG. 11 is a flowchart illustrating a method 400 of preparing for a surgical procedure, in accordance with some embodiments. At step 402, a first surgical guide, such a surgical guide 302a, is removed from a surgical guide carrier, such as, for example, a continuous roll guide carrier 200, a sheet guide carrier 300, a backing (not shown), and/or any other suitable surgical guide carrier. Although embodiments are discussed herein with respect to surgical guide 2, it will be appreciated that the method 400 can utilize any of the surgical guides 2-2j disclosed herein. At step 404, the first surgical guide 302a is positioned at a predetermined surgical site and affixed to a patient, such as, for example, a predetermined portion of a patient's foot.

At optional step 406, a second surgical guide 302b is removed from a surgical guide carrier. The surgical guide carrier may be the same guide carrier that previously included the first surgical guide carrier 302a and/or may be a different guide carrier, such as a separate backing, continuous roll guide carrier, sheet guide carrier, etc. At optional step 408, the second surgical guide 302b is coupled to a second surgical site, such as, for example, a second portion of a patient's foot. The second surgical site may be related to and/or separate from the first surgical site. In some embodiments, the second surgical guide 302b is placed adjacent and/or in relation to the first surgical guide 302a such that the first and second surgical guides 302a, 302b define a single surgical operation and/or surgical path. In some embodiments, the second surgical guide 302b is placed without relation to the first surgical guide 302a such that the first surgical guide 302a corresponds to at least a portion of a first surgical procedure and the second surgical guide 302b corresponds to at least a portion of a second surgical procedure.

At step 410, a fluoroscopic and/or other medical image is obtained of the surgical site including the first surgical guide 302a and/or the second surgical guide 302b. The fluoroscopic image is used to confirm the position of the surgical guide(s) 302a, 302b with respect to at least one anatomical structure, such as, for example, one or more bones of a patient's foot, hand, or other extremity. In some embodiments, a radiopaque guide element 30 formed integrally with a surgical guide 302a, 302b identifies a position of the surgical guide 302a, 302b with respect to the anatomical structure on the fluoroscopic image. The fluoroscopic image may be used to confirm a surgical path as illustrated by a radiopaque guide element 30, confirm positioning of a surgical guide 302a, 302b to be used in a surgical procedure, confirm a position of an incision guard 20 formed integrally with the surgical guide 302a, and/or confirm position of anatomical structures prior to conducting a surgical procedure. At optional step 412, one or more of the surgical guide(s) 302a, 302b are removed from the surgical site and repositioned, for example, based on the fluoroscopic image.

At optional step 414, one or more of the surgical guides 302a, 302b are removed from a surgical site. For example, in some embodiments a surgical guide 302a may be used solely for pre-operative planning and imaging and may be removed prior to performing one or more surgical procedures.

At step 416, one or more surgical procedures are performed based on and/or corresponding to a location indicated by and/or overlapping with one or more of the surgical guides 302a, 302b. In some embodiments, the first surgical guide 302a and/or the second surgical guide 302b includes an incision guard 20 sized and configured to receive a surgical instrument therethrough. A surgical instrument, such as a burr or other cutting instrument, is inserted through the incision guard 20 to perform a surgical operation, such as a skin incision and/or bone cutting operation. In some embodiments, a radiopaque guide element 30 defined on and/or formed integrally with the surgical guide 302a, 302b is configured to provide guidance to and/or mark a location for formation of an incision, osteotomy, or other surgical procedure.

At step 418, the surgical guide(s) 302a, 302b may be removed from the surgical site(s) and additional portions of a procedure and/or additional procedures may be performed. For example, in some embodiments, an osteotomy procedure may be completed after the surgical guides 302a, 302b are removed from the surgical site.

Although the subject matter has been described in terms of exemplary embodiments, it is not limited thereto. Rather, the appended claims should be construed broadly, to include other variants and embodiments, which may be made by those skilled in the art.

What is claimed is:

1. A surgical guide, comprising:
a flexible body defined by a first side, a second side, and an outer perimeter, wherein an adhesive material is disposed over at least a portion of the first side;
a radiopaque guide element coupled to the second side of the body; and
an incision guard defining an opening extending from the first side to the second side of the body, the incision guard sized and configured to receive a surgical instrument therethrough, wherein the incision guard includes an eyelet configured to provide reinforcement to the body and defining an inner perimeter of the opening, and is configured to prevent contact between the surgical instrument and a portion of a surgical site adjacent to the opening.

2. The surgical guide of claim 1, wherein the radiopaque guide element comprises a linear guide element.

3. The surgical guide of claim 1, wherein the radiopaque guide element comprises a curved guide element.

4. The surgical guide of claim 1, wherein the radiopaque guide element comprises an angled guide element having a first portion disposed at a predetermined angle with respect to a second portion.

5. The surgical guide of claim 4, wherein the incision guard is located at an intersection of the first portion and the second portion of the radiopaque guide element.

6. The surgical guide of claim 1, wherein the opening defined by the incision guard extends at least partially through the radiopaque guide element.

7. The surgical guide of claim 1, wherein the eyelet is a radiopaque eyelet.

8. The surgical guide of claim 1, wherein the radiopaque guide element is configured to correspond to a position of at least one anatomical structure of a patient when the body is coupled to a patient, and wherein the incision guard is configured to guide the surgical instrument to the at least one anatomical structure.

9. A system, comprising:
a surgical guide carrier;
a first surgical guide coupled to the surgical guide carrier in a first position, wherein the first surgical guide comprises:

a flexible body defined by a first side, a second side, and an outer perimeter, wherein an adhesive material is disposed over at least a portion of the first side;

a radiopaque guide element coupled to the second side of the body; and an incision guard defining an opening extending from the first side to the second side of the body, the incision guard sized and configured to receive a surgical instrument therethrough, wherein the incision guard includes an eyelet configured to provide reinforcement to the body and defining an inner perimeter of the opening, and is configured to prevent contact between the surgical instrument and a portion of a surgical site adjacent to the opening; and a second surgical guide coupled to the surgical guide carrier in a second position, wherein the second surgical guide comprises:

a body having a first side and a second side, wherein an adhesive material is disposed over at least a portion of the first side; and a radiopaque guide element coupled to a second side of the body.

10. The system of claim 9, wherein the surgical guide carrier comprises material configured to couple the first surgical guide to the second surgical guide in a continuous relationship.

11. The system of claim 9, wherein the surgical guide carrier comprises a sheet having a first surface configured to be coupled to the first surgical guide and the second surgical guide.

12. The system of claim 9, wherein the radiopaque guide element of the first surgical guide comprises a linear guide element.

13. The system of claim 9, wherein the radiopaque guide element of the first surgical guide comprises a curved guide element.

14. The system of claim 9, wherein the radiopaque guide element of the first surgical guide comprises an angled guide element having a first portion disposed at a predetermined angle with respect to a second portion.

15. The system of claim 14, wherein the incision guard is located at an intersection of the first portion and the second portion of the radiopaque guide element.

16. The system of claim 9, wherein the opening defined by the incision guard extends at least partially through the radiopaque guide element of the first surgical guide.

17. The system of claim 9, wherein eyelet is a metal eyelet.

18. A method, comprising:

removing a first surgical guide from a carrier, wherein the first surgical guide comprises a flexible body defined by a first side, a second side, and an outer perimeter, the first side including an adhesive material disposed over at least a portion thereof and the second side, a radiopaque guide element coupled to the second side of the body, and an incision guard defining an opening extending from the first side to the second side of the body, including an eyelet configured to provide reinforcement to the body and defining an inner perimeter of the opening, and configured to receive a surgical instrument therethrough;

coupling the first surgical guide to a first surgical site;

obtaining a fluoroscopic image of the first surgical site including the first surgical guide;

inserting the surgical instrument through the incision guard to perform at least one surgical procedure, wherein the incision guard is configured to prevent contact between the surgical instrument and a portion of the first surgical site located adjacent to the opening defined by the incision guard.

19. The method of claim 18, comprising coupling a second surgical guide to a second surgical site prior to obtaining the fluoroscopic image, wherein the second surgical guide comprises a body and a radiopaque guide element.

20. The method of claim 18, comprising:

removing the first surgical guide from the first surgical site prior to inserting the first surgical instrument through the incision guard;

coupling the first surgical guide to an alternative surgical site selected based on the obtained fluoroscopic image; and obtaining an additional fluoroscopic image of the alternative surgical site including the first surgical guide.

* * * * *